United States Patent
Burke, Jr. et al.

[11] Patent Number: 5,113,528
[45] Date of Patent: May 19, 1992

[54] FACE SHIELD

[76] Inventors: John W. Burke, Jr., 36 E. Wyoming Ave., Melrose, Mass. 02176; Peter J. Gazzara, 8 Woodbine St., Reading, Mass. 01867

[21] Appl. No.: 464,297

[22] Filed: Jan. 12, 1990

[51] Int. Cl.⁵ .......................... A42B 1/06; A61F 9/04
[52] U.S. Cl. ............................................ 2/9; 2/181.8; 2/424; 128/857
[58] Field of Search .......... 2/9, 15, 410, 424, DIG.11, 2/181.8, 431, 433; 128/857, 858

[56] References Cited

U.S. PATENT DOCUMENTS

| | | | |
|---|---|---|---|
| D. 318,477 | 7/1991 | Russell | D29/16 |
| 1,170,052 | 2/1916 | Diener et al. | 2/181.6 |
| 1,337,036 | 4/1920 | Bergmann . | |
| 1,923,340 | 8/1933 | Steckler . | |
| 2,907,041 | 10/1959 | Finn . | |
| 4,646,367 | 3/1987 | El Hassen | 2/DIG. 11 |
| 4,825,878 | 5/1989 | Kuntz et al. | 128/857 |
| 4,852,185 | 8/1989 | Olson | 2/9 |
| 4,852,189 | 8/1989 | Duggan | 2/15 |
| 4,864,653 | 9/1989 | Landis | 2/9 |
| 4,872,465 | 10/1989 | Kuntz et al. | 2/9 |
| 4,884,296 | 12/1989 | Nix, Jr. | 2/9 |
| 4,910,804 | 3/1990 | Ledgren | 2/181.8 |
| 4,920,576 | 5/1990 | Landis | 2/9 |
| 4,944,312 | 7/1990 | Smith | 128/857 |

OTHER PUBLICATIONS

Actual polaroid picture of face shield labeled "A". (Date unknown).
Actual polaroid picture of face shield labeled "B". (Date unknown).
Actual polaroid picture face shield labeled "C". (Date unknown).
Actual polaroid Picture of a face shield labeled "D". (Date unknown).
Actual polaroid picture of a face shield labeled "E". (Date unknown).
Actual polaroid picture of a face shield labeled "E". (Date unknown).
Actual polaroid picture of a face shield labeled "F". (Date unknown).

*Primary Examiner*—William A. Cuchlinski, Jr.
*Assistant Examiner*—C. W. Fulton

[57] ABSTRACT

Face shield for protecting a wearer's face from spatters. The shield includs a flexible, transparent portion sized to cover the face and a flexible spacer portion for contact with the wearer's forehead to provide adequate clearance of the transparent flexible portion away from the wearer's face. When worn, the flexible spacer portion substantially completely seals the top portion of the shield to prevent spatters from reaching the face from the top, that is, through the portion occupied by the spacer.

5 Claims, 2 Drawing Sheets

FACE SHIELD

BACKGROUND OF THE INVENTION

This invention relates to a shield to protect the face, especially from spattered fluids.

Liquids often spatter and come in contact with the face. While painting a ceiling, for example, a painter often finds that his face is flecked with spattered paint. During medical procedures, medical personnel are often subject to blood and other bodily fluids coming into contact with the face. Such contact is dangerous because of the potential presence of the deadly AIDS virus or other harmful pathogens.

FIG. 1 is a prior art face shield distributed by the Safe-T-Face Corporation of Beverly Hills, Calif. With reference to FIG. 1, a prior art disposable face shield 10 includes a transparent member 12 affixed to a cardboard framework 14 which folds flat for shipment and which expands to the configuration shown in FIG. 1 when worn by a person whose face is to be protected. The shield 10 is secured to a wearer (not shown) by an elastic band 16. Importantly, when worn the cardboard framework 14, which supports the transparent member 12 away from the face, creates a large gap 18 between a wearer's forehead and the front of the transparent member 12. Thus, spatters can travel through the wide gap 18 and land on the wearer's face. That is to say, the prior art face shield 10 will afford protection only from fluid spatters approaching the face from the front. On the other hand, spatters approaching the top of the head will readily pass through the gap 18 and land on the wearer's face.

SUMMARY OF THE INVENTION

The face shield according to the present invention includes a flexible, fluid impervious, transparent member sized to cover a human face. A flexible barrier and spacer member is affixed to a top portion of the transparent member and apparatus is provided for securing the transparent member/spacer member combination to the human face with the spacer member in contact with the forehead of the face. The barrier and spacer member creates a barrier between the forehead and the transparent member so as to prevent fluids approaching the head from the top from reaching the face.

In a preferred embodiment, the spacer member includes scallops proximate the forehead to facilitate comformance of the spacer with the forehead when worn. The spacer member is preferably pervious to air for the comfort of the wearer, but substantially impervious to liquid spatters. In this embodiment, the securing apparatus includes an elastic band. This band may be affixed to the transparent member or to the spacer member. It is preferred that the transparent member be made of a thin flexible plastic material and it is preferred that the spacer member be foam plastic.

Because the face shield of the invention employs a barrier and spacer member, spatters approaching the top of the head are prevented from contacting the wearer's face. This is unlike the known prior art device which affords no protection for spatters approaching the head from this direction.

DESCRIPTION OF THE PREFERRED EMBODIMENT

Figure 1:
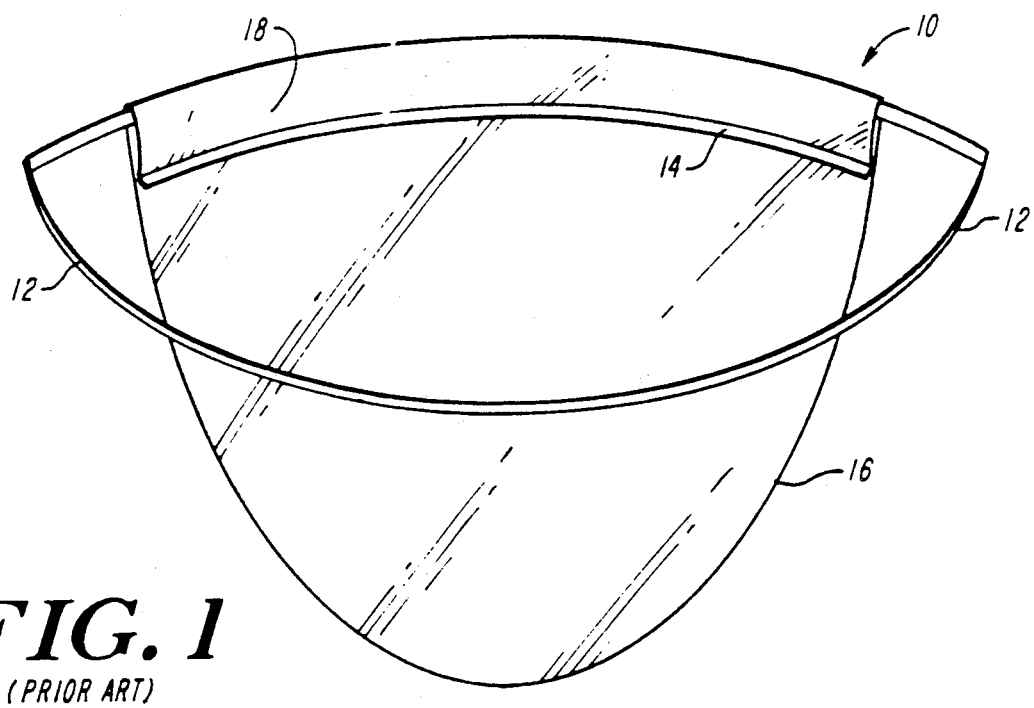
FIG. 1 is a perspective view of a prior art face shield.
Figure 2:
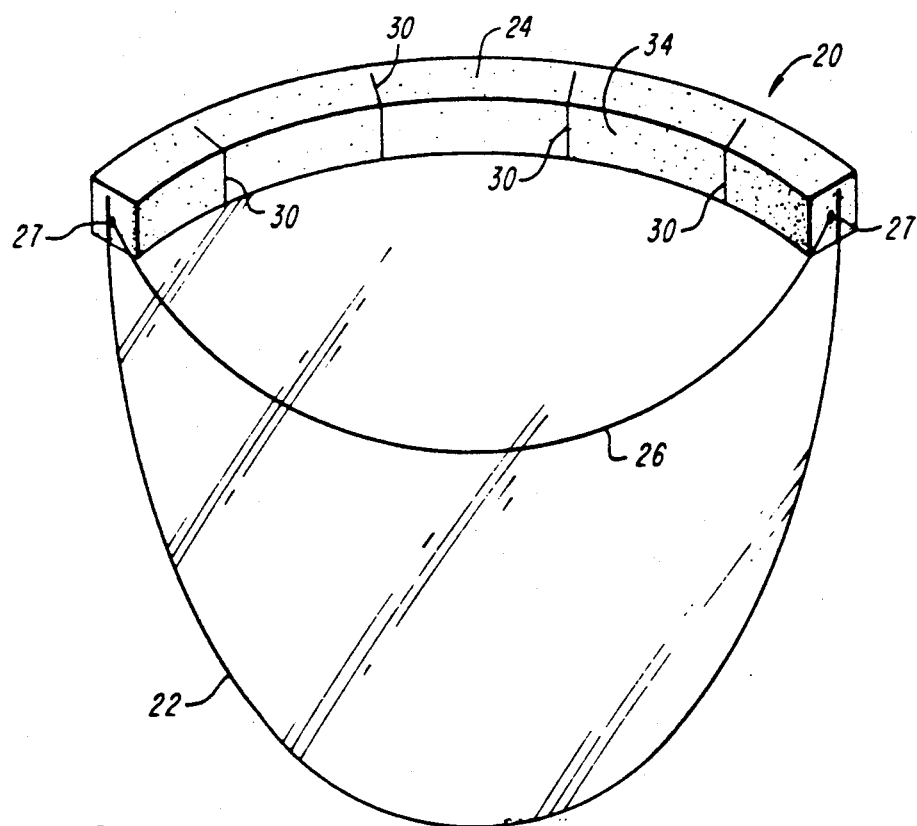
FIG. 2 is a perspective view of the face shield of the present invention.

With reference now to FIG. 2, a face shield 20 according to the invention includes a flexible, fluid impervious, transparent member 22 sized generally to cover a human face. Affixed to the top portion of the transparent member 22 by a suitable adhesive is a barrier and spacer member 24 which serves to space the transparent member 22 away from the face when the shield is being worn so that the member 22 does not rest, for example, against the nose which would result in discomfort to the wearer. As will be described in detail hereinbelow, the member 24 also serves as a barrier to the passage of fluids. An elastic band 26 is affixed either to the transparent member 22 or the spacer member 24 and serves to support the face shield 20 on the wearer's head with a forehead engaging surface 34 of the spacer member 24 in contact with the wearer's forehead. It is advantageous that the elastic band 26 be attached at a location 27 below a center line of the spacer member 24 so that the shield 20 is urged toward the face when worn.

Figure 3:
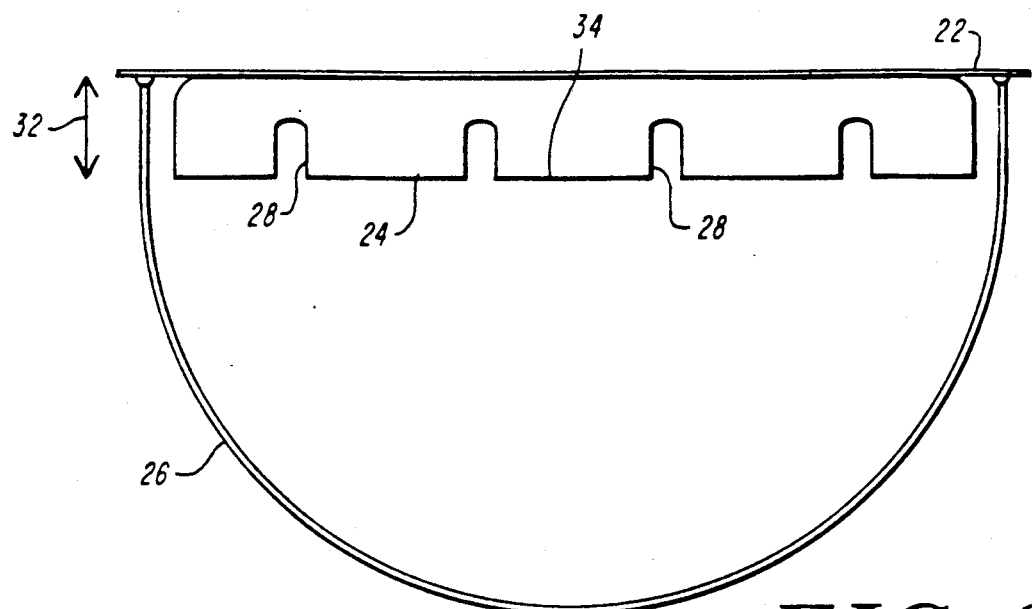
FIG. 3 is a top view of the shield of the invention.

As shown in FIG. 3, it is preferred that the spacer member 24 have a series of scallops 28 extending into the spacer member from the forehead engaging surface 34 to facilitate bending to conform with a wearer's forehead. The scallops can be die cut into the foam plastic. The scallops close completely when worn, as shown by the lines 30 in FIG. 2, to serve as an effective barrier. An appropriate spacer dimension shown by an arrow 32 in FIG. 3 is approximately 1¾ inches.

Figure 4:
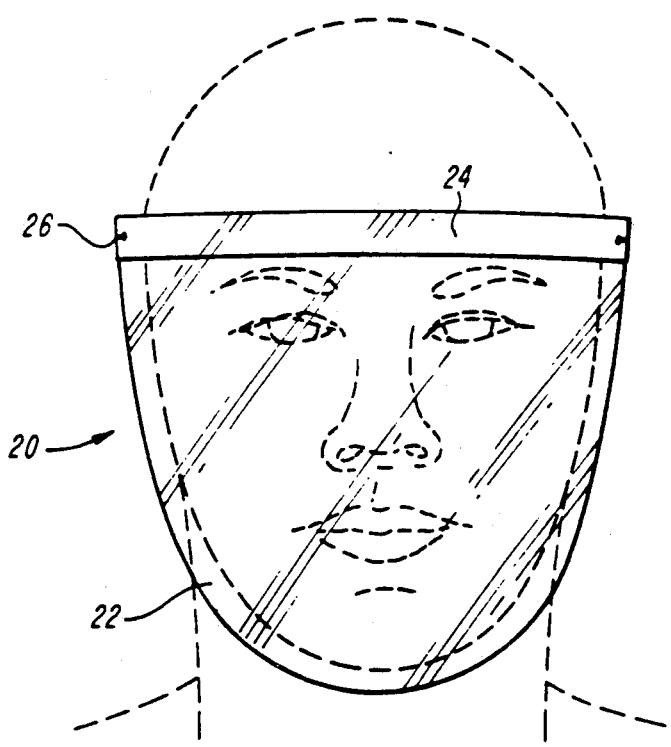
FIG. 4 is a front view of the shield of the invention.

As shown in FIG. 4, the face shield 20 is worn with the spacer member 24 in contact with a wearer's forehead. The elastic band 26 encircles the head to hold the shield in place. When in place on the head, the spacer member 24 bends to conform with the curvature of the forehead and the scallops 28 completely close so that a solid barrier is provided to prevent fluids approaching from the top of the head direction from intersecting the face of a wearer. It is preferred that the spacer member be made of a material, such as foam plastic, which allows the passage of air but which is substantially impervious to the passage of liquid spatters. The passage of air through the spacer member reduces any tendency for fogging of the transparent member. In addition, small holes (not shown) can be made in the spacer member 24 to enhance air flow, but the holes should have a small size and angle so as not to permit spatters to pass through.

It is preferred that the transparent member 22 be made of polyester having a thickness of no less than five mils. A suitable material is available from Transilwrap Corporation of Elmwood, N.J. It is also preferred that the spacer and barrier member 24 be a foam plastic material such as white polyether having a 1.2 pound density. Those skilled in the art will readily appreciate that other materials may be utilized.

What is claimed is:

1. Face shield comprising:
   a flexible, fluid impervious, transparent member sized to cover a human face;
   a flexible barrier and spacer member affixed to a top portion of the transparent member, the barrier and spacer member substantially spanning the full extent of the transparent member and including
a foam plastic material.
a forehead engaging surface,
a plurality of scallops extending into the barrier and spacer member from the forehead engaging surface; and
apparatus for securing the transparent member/barrier and spacer member combination to the human face so that the forehead engaging surface of the barrier and spacer member contacts the forehead of the face,
whereby when the transparent member/barrier and spacer combination is secured to the face, the scallops close so that the barrier and spacer member creates an air previous and a substantially liquid impervious barrier between the forehead and the transparent member.

2. The face shield of claim 1 wherein the securing apparatus comprises an elastic band.

3. The face shield of claim 2 wherein the band is affixed to the transparent member.

4. The face shield of claim 2 wherein
the elastic band is attached at a location below the center line of the barrier and spacer member.

5. The face shield of claim 1 wherein the transparent member is plastic.

* * * * *

UNITED STATES PATENT AND TRADEMARK OFFICE
CERTIFICATE OF CORRECTION

PATENT NO. : 5,113,528
DATED : May 19, 1992
INVENTOR(S) : John W. Burke, Jr., et al It is certified that error appears in the above-indentified patent and that said Letters Patent is hereby corrected as shown below:

On the title page, Abstract, line 2, change "includs" to "includes".

Signed and Sealed this

Seventh Day of September, 1993

Attest:

Attesting Officer

BRUCE LEHMAN

Commissioner of Patents and Trademarks